(12) United States Patent
Chaudhry

(10) Patent No.: US 10,987,476 B2
(45) Date of Patent: Apr. 27, 2021

(54) ANESTHESIA GAS DELIVERY AND MONITORING SYSTEM

(71) Applicant: H. LEE MOFFITT CANCER CENTER AND RESEARCH INSTITUTE, INC., Tampa, FL (US)

(72) Inventor: Tariq Chaudhry, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 17/004,808

(22) Filed: Aug. 27, 2020

(65) Prior Publication Data

US 2020/0390991 A1    Dec. 17, 2020

Related U.S. Application Data

(63) Continuation of application No. 16/378,141, filed on Apr. 8, 2019, which is a continuation-in-part of (Continued)

(51) Int. Cl.
*A61M 16/01* (2006.01)
*A61M 16/04* (2006.01)
(Continued)

(52) U.S. Cl.
CPC ........ *A61M 16/01* (2013.01); *A61M 16/0003* (2014.02); *A61M 16/0493* (2014.02);
(Continued)

(58) Field of Classification Search
CPC ........ A61M 2025/022; A61M 16/0488; A61M 16/049; A61M 16/0493; A61M 16/01; A61M 16/021; A61M 16/022; A61M 16/0096; A61M 16/024; A61M 16/026; A61M 16/0003; A61M 16/0006; A61M 16/0009; A61M 16/0012; A61M 16/0497; A61M 16/0495; A61M 16/0666; A61M 16/0672; A61M 16/0677; A61M 16/0683;
(Continued)

(56) References Cited

U.S. PATENT DOCUMENTS

| 2,644,234 A | * | 7/1953 | Scott | ............ A61C 17/08 433/94 |
| 2,840,070 A | * | 6/1958 | Tofflemire | ............ A61B 1/24 600/246 |

(Continued)

FOREIGN PATENT DOCUMENTS

WO    WO-2009134295 A1 * 11/2009 ............. A61C 17/08

*Primary Examiner* — Jan Christopher L Merene
*Assistant Examiner* — Brian T Khong
(74) *Attorney, Agent, or Firm* — Meunier Carlin & Curfman LLC

(57) ABSTRACT

Various implementations include a gas delivery and monitoring apparatus that can be used, for example, to deliver oxygen and monitor exhaled carbon dioxide in a subject while under anesthesia. One advantage of the disclosed apparatus is the ability to deliver oxygen directly to the back of the mouth instead of in front of the face. Another advantage of the disclosed apparatus over existing nasal cannulas is the ability to capture carbon dioxide exhaled from both the nose and mouth.

22 Claims, 9 Drawing Sheets

Related U.S. Application Data application No. 15/946,782, filed on Apr. 6, 2018, now Pat. No. 10,252,018, which is a continuation of application No. PCT/US2017/050249, filed on Sep. 6, 2017.

(60) Provisional application No. 62/383,849, filed on Sep. 6, 2016.

(51) Int. Cl.
 *A61M 16/00* (2006.01)
 *A61M 16/08* (2006.01)
 *A61M 16/06* (2006.01)

(52) U.S. Cl.
 CPC .... *A61M 16/0666* (2013.01); *A61M 16/0672* (2014.02); *A61M 16/085* (2014.02); *A61M 2202/0208* (2013.01); *A61M 2205/3327* (2013.01); *A61M 2209/088* (2013.01); *A61M 2210/0618* (2013.01); *A61M 2210/0625* (2013.01); *A61M 2230/432* (2013.01)

(58) Field of Classification Search
 CPC ............ A61M 16/0841; A61M 16/085; A61M 16/0858; A61C 17/08; A61C 5/90; A61J 15/0011; A61J 15/003–0046; A61J 15/0053–0065; A61B 90/16; A61B 1/32; A61B 17/02; A61B 17/30
 See application file for complete search history.

(56) References Cited

U.S. PATENT DOCUMENTS

| | | | | |
|---|---|---|---|---|
| 3,889,658 A * | 6/1975 | Newhall | ................ | A61D 13/00 600/549 |
| 3,924,333 A * | 12/1975 | Erickson | ................ | A61C 17/08 433/93 |
| 4,167,814 A * | 9/1979 | Schubert | ................ | A61C 17/08 433/93 |
| 4,198,967 A * | 4/1980 | Dror | ................ | A61M 16/0493 128/860 |
| 4,215,984 A * | 8/1980 | Reichley | ................ | A61C 17/08 433/93 |
| 4,365,162 A * | 12/1982 | Jarby | ................ | G03B 42/042 378/170 |
| 4,437,463 A * | 3/1984 | Ackerman | ........ | A61M 16/0488 128/207.17 |
| 4,605,990 A * | 8/1986 | Wilder | ................ | A61B 1/32 24/507 |
| 5,071,347 A * | 12/1991 | McGuire | ................ | A61C 17/08 433/91 |
| 5,078,602 A * | 1/1992 | Honoshofsky | ......... | A61C 17/08 433/91 |
| 5,152,686 A * | 10/1992 | Duggan | ................ | A61C 17/08 433/93 |
| 5,156,593 A * | 10/1992 | Green | ................ | A61D 7/00 119/72 |
| 5,386,821 A * | 2/1995 | Poterack | ........... | A61M 16/0493 128/200.26 |
| 5,588,836 A * | 12/1996 | Landis | ................ | A61C 17/08 433/93 |
| 5,655,519 A * | 8/1997 | Alfery | ................ | A61M 16/0488 128/200.24 |
| 5,660,168 A * | 8/1997 | Ottosson | ................ | G01K 1/14 128/200.24 |
| 5,827,061 A * | 10/1998 | Goodman | ............ | A61C 17/08 433/93 |
| 6,213,772 B1 * | 4/2001 | Costello | ................ | A61C 17/08 433/93 |
| 6,939,134 B2 * | 9/2005 | Sherry | ................ | A61C 5/90 433/140 |
| 7,946,288 B2 * | 5/2011 | Flynn | ................ | A61M 16/12 128/200.24 |
| 2007/0282272 A1 * | 12/2007 | Bannon | ............ | A61M 5/1418 604/174 |
| 2008/0053434 A1 * | 3/2008 | Wightman | ........ | A61M 16/0488 128/200.26 |
| 2008/0276941 A1 * | 11/2008 | Doty | ................ | A61M 16/009 128/205.28 |
| 2009/0274991 A1 * | 11/2009 | Black | ................ | A61C 17/08 433/93 |
| 2009/0283097 A1 * | 11/2009 | Niklewski | ............ | A61M 16/08 128/207.14 |
| 2011/0229847 A1 * | 9/2011 | Worthington | .......... | A61C 17/08 433/93 |
| 2011/0270166 A1 * | 11/2011 | Martin | ................ | A61H 21/00 604/79 |
| 2013/0327901 A1 * | 12/2013 | Fristoe | ............. | A61M 16/0672 248/75 |
| 2014/0000626 A1 * | 1/2014 | O'Connor | ......... | A61M 16/0666 128/207.18 |
| 2014/0261413 A1 * | 9/2014 | Gibson | ............ | A61M 16/0683 128/203.12 |
| 2014/0276171 A1 * | 9/2014 | Hestness | ........... | A61M 16/0493 600/531 |
| 2015/0099993 A1 * | 4/2015 | Weaver | ................ | A61B 5/4839 600/531 |
| 2016/0220777 A1 * | 8/2016 | Weaver | ................ | A61B 5/4839 |
| 2016/0270878 A1 * | 9/2016 | Fulton, III | ................ | A61B 1/24 |
| 2016/0310234 A1 * | 10/2016 | Ritter | ................ | A61B 1/32 |

* cited by examiner

ANESTHESIA GAS DELIVERY AND MONITORING SYSTEM

CROSS-REFERENCE TO RELATED APPLICATIONS

This application is a continuation of U.S. application Ser. No. 16/378,141, filed Apr. 8, 2019, which is a continuation-in-part of U.S. application Ser. No. 15/946,782, filed Apr. 6, 2018, which is a continuation of PCT/US2017/050249, filed Sep. 6, 2017,which claims the benefit of U.S. Provisional Application No. 62/383,849, filed Sep. 6, 2016, of which are incorporated herein by reference in their entireties.

BACKGROUND

Approximately 200,000,000 sedation procedures are performed in the U.S every year. Patient monitoring during sedation procedures can require the use of a nasal cannula with the prongs inserted into the nostrils to deliver oxygen while monitoring exhaled carbon dioxide. A wide range of issues from inaccurate monitoring to patient injury make this setup unreliable with significant room for improvement.

Nasal insertion of the prongs in patients with oral breathing often leads to a cascade of monitoring issues. Moving the nasal prongs into the patient's mouth is unhygienic but performed regularly in the absence of a better option. Nasal cannulas are insecure and often get dislodged causing loss of carbon dioxide capture as well as inability to deliver oxygen into the nostrils. During facial procedures, nasal cannulas get in the sterile surgical field causing a risk for surgical infections.

Oxygen is heavier than air and tends to settle around the face. Every year several hundred cases of surgical fires causing patient injury are reported when an electrocautery is used. Electrocautery causes sparks and oxygen acts as fuel.

Approximately two million patients in the U.S are on oxygen therapy either at home or in the nursing homes. Oxygen is delivered through a nasal cannula which is connected to a portable oxygen tank. These patients encounter multiple issues. Nasal cannula tubing has a large surface area that comes in contact with facial skin and long-term use can cause skin irritation, dermatitis or skin ulcers. Continuous oxygen flow through the nostrils can cause mucosal dryness. As prevention, humidifier bottles are added but water vapor condensation not only blocks the oxygen flow to the patient, it can also promote bacterial growth in the tubing. Part of the oxygen delivery through the nasal prongs gets wasted during breath exhalation. A typical oxygen tank lasts 4-5 days. It is estimated that 40-60% of the patients on home oxygen therapy continue to smoke. Lighter flame in close proximity to the plastic prongs emitting oxygen causes serious injuries, death and loss of property each year in the U.S. Therefore, the current nasal cannula lacks appropriate safety and reliability.

SUMMARY

Disclosed herein is a gas delivery and monitoring apparatus that can be used, for example, to deliver oxygen and monitor exhaled carbon dioxide in a subject while under anesthesia. One advantage of the disclosed apparatus is the ability to deliver oxygen directly to the back of the mouth instead of in front of the face. Another advantage of the disclosed apparatus over existing nasal cannulas is the ability to capture carbon dioxide exhaled from both the nose and mouth.

The disclosed apparatus comprises a support member having a channel therewithin extending along a longitudinal axis from a proximal end of the channel to a distal end of the channel, and a bite block affixed to the support member sized to be inserted within a mouth of a subject.

The disclosed apparatus also comprises a first elongated conduit defining an exhalation capture flow path extending from an exhalation capture manifold, through the channel from the distal end to the proximal end, and terminating in an outlet port. In particular embodiments, the exhalation capture manifold captures air exhaled from a subject, which travels through the first elongated conduit to the outlet port, where it is connected to a carbon dioxide monitoring system (capnograph). The exhalation capture manifold preferably contains a first capture inlet and a second capture inlet each fluidly connected to the exhalation capture manifold. This allows for one inlet to be positioned for capture of exhalation from the nose, while another inlet is positioned for exhalation by the mouth. Therefore, in particular embodiments, the first capture inlet and a second capture inlet have perpendicular flow paths.

The disclosed apparatus also comprises a second elongated conduit defining a gas delivery flow path extending from an inlet port, through the channel from the proximal end to the distal end, into the bite block, and terminating in a gas delivery port. In particular embodiments, the inlet port is connected to an oxygen source, which delivers oxygen through the second elongated conduit to the gas delivery port. Therefore, in some embodiments of the apparatus, the inlet port is fluidly-connectable to a source of pressurized oxygen.

Oxygen exits the delivery port for inhalation by the subject. The delivery port is positioned by the bite block within the mouth instead of in front of the face. In some cases, the second elongated conduit extends through and past the bite block to terminate in the gas delivery port (i.e., the gas delivery port extends past the bite block). In other embodiments, the bite block further comprises an outlet manifold fluidly connected to the gas delivery port.

The remaining dimensions of the first elongated conduit and second elongated conduit relative to the support member and bite block can be selected based on anatomical needs. For example, in some embodiments, the distance between the distal end of the channel and the exhalation capture manifold is about 4 to 8 cm.

Various other embodiments include a gas delivery and monitoring apparatus having a support member, a bite block, a first elongated conduit, a second elongated conduit, and a bridge. The support member has a longitudinal axis. The bite block is affixed to the support member and is sized to be inserted within a mouth of a subject. The first elongated conduit defines an exhalation capture flow path extending from a capture inlet at the distal end of the bite block and terminating in an outlet port. The second elongated conduit defines a gas delivery flow path extending from an inlet port into the bite block and terminating in a gas delivery port at the distal end of the bite block. Both the gas delivery port and capture inlet are located in the mouth of the subject when the bite block is inserted in the mouth of the subject during use. The bridge connects the bite block to the support member. The bridge extends away from the support member. The bridge positions the bite block a first minimum distance from the support member such that the support member and the bite block are simultaneously positionable on opposite sides of a cheek of a subject.

In some embodiments, the support member has a channel therewithin extending along the longitudinal axis from a proximal end of the channel to a distal end of the channel.

In some embodiments, the apparatus further includes a third elongated conduit defining a nasal exhalation capture flow path extending from a secondary capture inlet, through the channel from the distal end to the proximal end, and terminating in an outlet port.

In some embodiments, the first elongated extends through the channel from the proximal end to the distal end. In some embodiments, the second elongated conduit extends through the channel from the proximal end to the distal end.

In some embodiments, the bridge extends away from the support member along a transverse plane perpendicular to the longitudinal axis. The bridge positions the bite block a first minimum distance from the support member. In some embodiments, the first minimum distance is 1 to 3 cm. In some embodiments, the bridge is deformable to a second minimum distance from the support element. In some embodiments, the second minimum distance is 1 to 3 cm. In some embodiments, the bridge provides spring tension to secure the bite block within the mouth of the subject.

In some embodiments, the second elongated conduit extends through the bite block to terminate in the gas delivery port.

In some embodiments, the first elongated conduit includes a flexible elastomeric material that is not gas-permeable.

In some embodiments, the third elongated conduit is encased in a deformable sheath.

In some embodiments, the second elongated conduit comprises a flexible elastomeric material that is not gas-permeable.

In some embodiments, the inlet port is fluidly-connectable to a source of pressurized oxygen.

In some embodiments, at least a portion of each of the support member, bite block, and bridge are integrally formed. In some embodiments, the support member, bite block, and bridge are mechanically connected.

In some embodiments, a distance between the distal end of the channel and the secondary capture inlet is about 4 to 8 cm.

In some embodiments, the first elongated conduit has an inner diameter of about 2 to 4 mm. In some embodiments, the second elongated conduit has an inner diameter of about 2 to 8 mm. In some embodiments, the third elongated conduit has an inner diameter of about 2 to 4 mm.

In some embodiments, the third elongated conduit comprises a flexible elastomeric material that is not gas-permeable.

The details of one or more embodiments of the invention are set forth in the accompanying drawings and the description below. Other features, objects, and advantages of the invention will be apparent from the description and drawings, and from the claims.

DETAILED DESCRIPTION

The present invention now will be described more fully hereinafter with reference to specific embodiments of the invention. The invention can be embodied in many different forms and should not be construed as limited to the embodiments set forth herein; rather, these embodiments are provided so that this disclosure will satisfy applicable legal requirements.

As used in the specification, and in the appended claims, the singular forms "a," "an," "the," include plural referents unless the context clearly dictates otherwise.

The term "comprising" and variations thereof as used herein are used synonymously with the term "including" and variations thereof and are open, non-limiting terms.

The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

Figure 1:
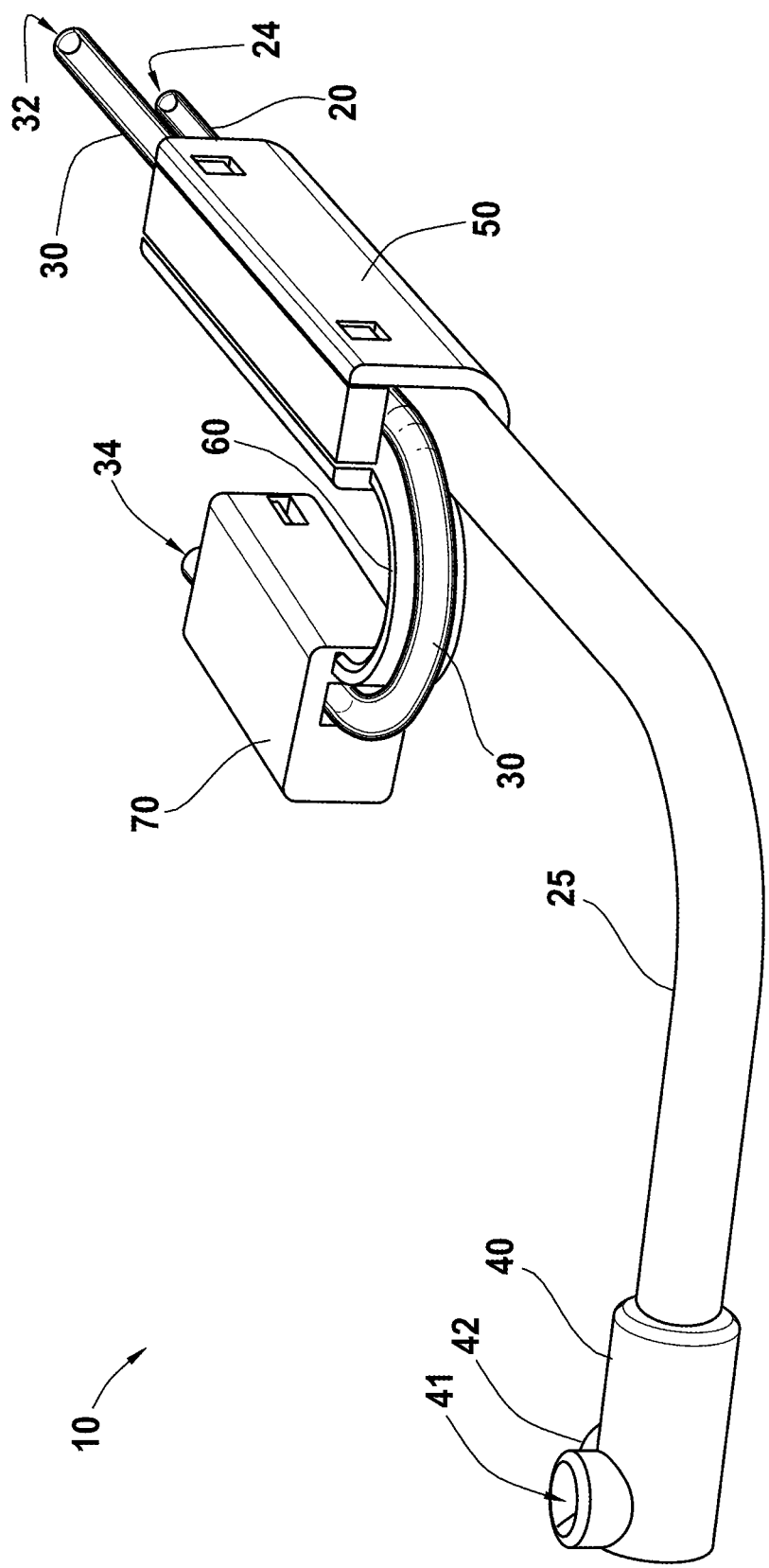
FIG. 1 is a perspective view of a gas delivery and monitoring apparatus according to one implementation.
Figure 2:
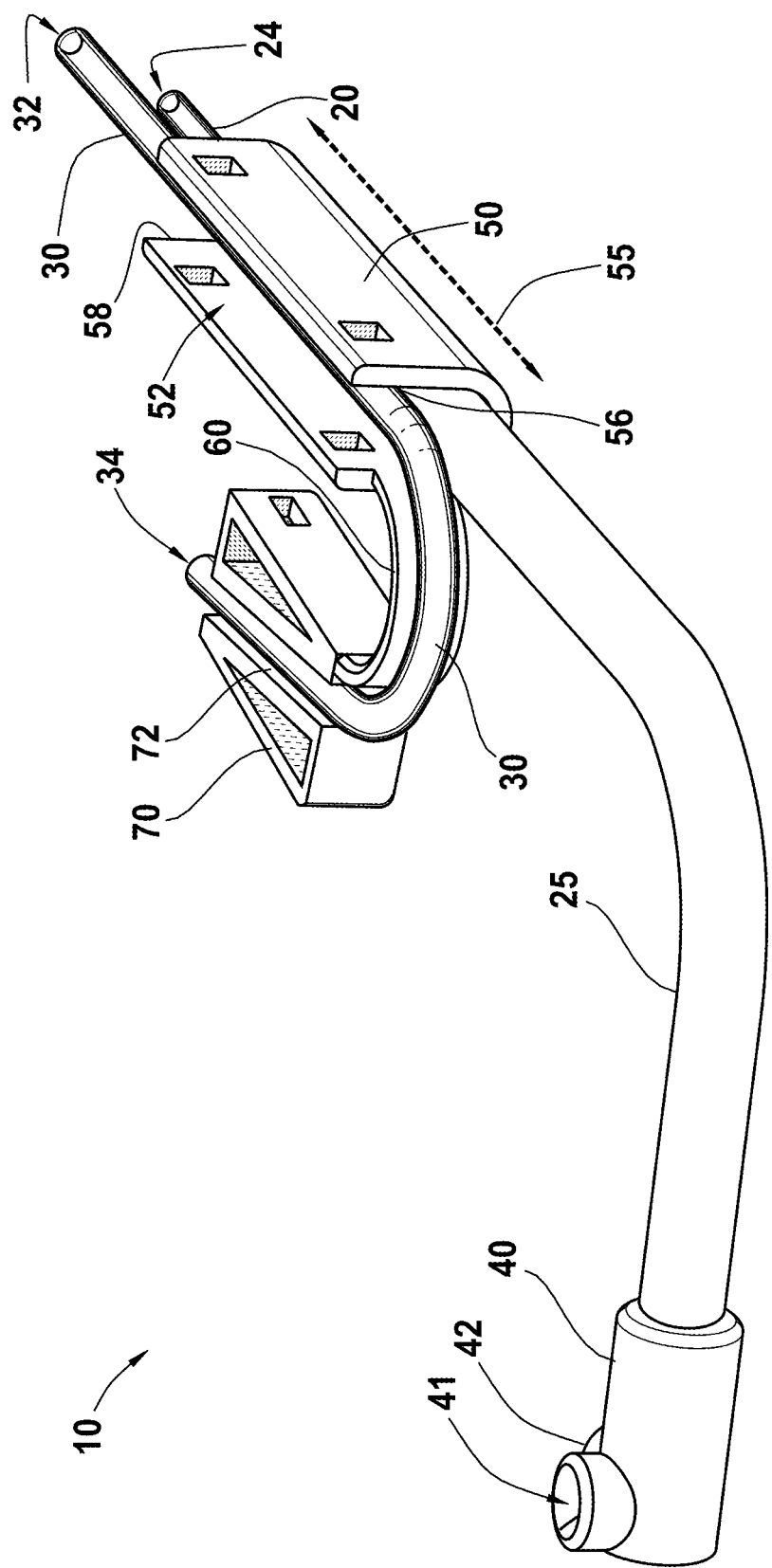
FIG. 2 is a cutout view of a gas delivery and monitoring apparatus according to one implementation.
Figure 3:
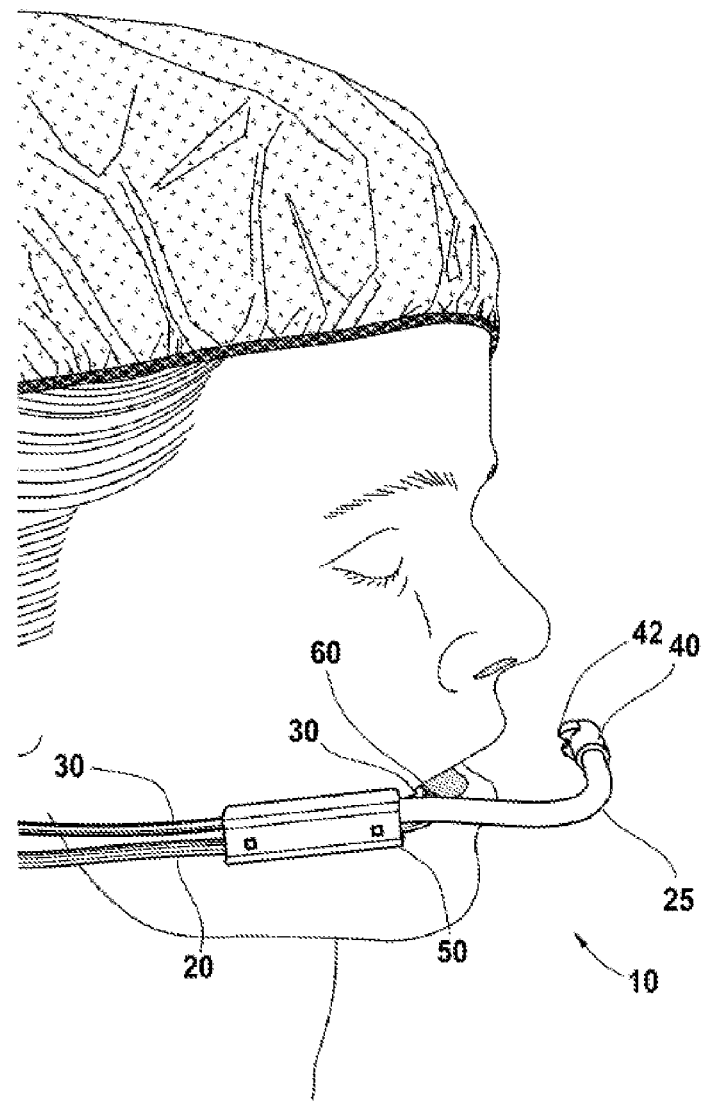
FIG. 3 is an illustration of a gas delivery and monitoring apparatus according to one implementation positioned in the mouth of a subject.

Now referring more particularly to FIGS. 1 and 2 of the drawings, a gas delivery and monitoring apparatus 10 is provided that can be used, for example, to deliver oxygen and monitor exhaled carbon dioxide in a subject while under anesthesia. As shown in FIGS. 1 and 2, the disclosed gas delivery and monitoring apparatus 10 has a first elongated conduit 20 for capturing exhalation from a subject and a second elongated conduit 30 for delivering gas to the subject for inhalation.

The first elongated conduit 20 defines an exhalation capture flow path extending from an exhalation capture manifold 40 to an outlet port 24. In particular embodiments, the exhalation capture manifold 40 captures air exhaled from a subject, which travels through the first elongated conduit to the outlet port 24, where it is connected to a carbon dioxide monitoring system (capnograph). The exhalation capture manifold 40 preferably contains a first capture inlet 41 and a second capture inlet 42 each fluidly connected to the exhalation capture manifold 40. This allows for one inlet to be positioned for capture of exhalation from the nose, while another inlet is positioned for exhalation by the mouth. Therefore, in particular embodiments, the first capture inlet 41 and a second capture inlet 42 have perpendicular flow paths. As shown in FIGS. 1 and 2, the first elongated conduit 20 can be inside a deformable sheath 25, allowing the exhalation capture manifold 40 to be positioned in front of the subject's nose and mouth.

The second elongated conduit 30 defines a gas delivery flow path extending from an inlet port 32 to a gas delivery port 34. In particular embodiments, the inlet port 32 is connected to an oxygen source, which delivers oxygen through the second elongated conduit 30 to the gas delivery port 34. Therefore, in some embodiments of the apparatus, the inlet port 32 is fluidly-connectable to a source of pressurized oxygen.

As shown in FIGS. 1 and 2, the disclosed gas delivery and monitoring apparatus 10 has a support member 50 having a channel 52 therewithin extending along a longitudinal axis 55 from a proximal end of the channel 58 to a distal end of the channel 56. The support member 50 is affixed to a bite block 70 that is sized to be inserted within a mouth of a subject.

As shown in FIG. 2, the first elongated conduit 20 extends from the exhalation capture manifold 40 through the channel 52 from the distal end 56 to the proximal end 58, and terminating in the outlet port 24.

The second elongated conduit 30 extends from the inlet port 32, through the channel 52 from the proximal end 58 to the distal end 56, into the bite block 70, and terminating in the gas delivery port 34. As depicted in FIG. 2, the second elongated conduit 30 can extend through a receiving element 72 (such as a channel) in the bite block. In some cases, the gas delivery port 34 extends past the bite block 70. In other embodiments, the bite block 70 further comprises an outlet manifold fluidly connected to the gas delivery port 34.

The support member 50 and bite block 70 are preferably configured so that they are positioned on opposite sides of a subject's cheek. As depicted in FIGS. 1 and 2, a bridge 60 can connect the bite block 70 to the support member 50. For example, the bridge 60 can extend away from the support member 50 along a transverse plane perpendicular to the longitudinal axis 55, wherein the bridge positions the bite block a first minimum distance from the support element. This distance is based on the thickness of a subject's cheek. Therefore, in some embodiments, this first minimum distance is about 1 to 3 cm, including about 1.0, 1.5, 2.0, 2.5, or 3.0 cm. The bridge is also preferably deformable to a second minimum distance from the support element to adjust for the size and shape of the subject's mouth and cheek. In these embodiments, the deformable distance (in a direction away from the support member) can be about 0.1 to 2 cm. In some embodiments, deformation of the bridge 60 also provides spring tension to secure the bite block 70 within the mouth of the subject. In some embodiments, at least a portion of each of the support member, bite block, and bridge are integrally formed. In some embodiments, the support member, bite block, and/or bridge are mechanically connected.

The bite block 70 can be a modular embodiment with adjustable heights to accommodate various size mouth openings. The bite block 70 can also have openings/ports to sample oral $CO_2$.

Each of the first elongated conduit 20 and second elongated conduit 30 can be made from a flexible elastomeric material that is not gas-permeable. Either of these conduits can also be coated or sheathed with another material to provide additional properties, such as rigidity and deformability. In particular embodiments, the first elongated conduit is encased in a deformable sheath 25 that can be articulated. In some embodiments, the sheath 25 is a plastic tube with a co-extruded metal wire that allows the tube to be bent and hold its shape.

Each of the support member 50, bridge 60, and bite block 70 can be made, in whole or in part, from a rigid material, such as a metal or plastic.

The inner diameters of the first and second elongated conduits can be selected based on desired air pressures. For example, in some embodiments, the first elongated conduit has an inner diameter of about 2 to 4 mm. In some embodiments, the second elongated conduit has an inner diameter of about 2 to 8 mm.

The outlet port and inlet port can each independently be any length past the proximal end of the channel, i.e., for connection to a carbon dioxide monitor and oxygen source, respectively. In some cases, the outlet port and/or inlet port are connected to a fitting, such as a luer tube fitting (e.g. male or female). In these cases, the apparatus can be connected to carbon dioxide monitor and oxygen source by extension tubing.

Optionally, the gas delivery and monitoring apparatus 10 can be sterilized, for example by chemical and/or heat based techniques.

Figure 4:
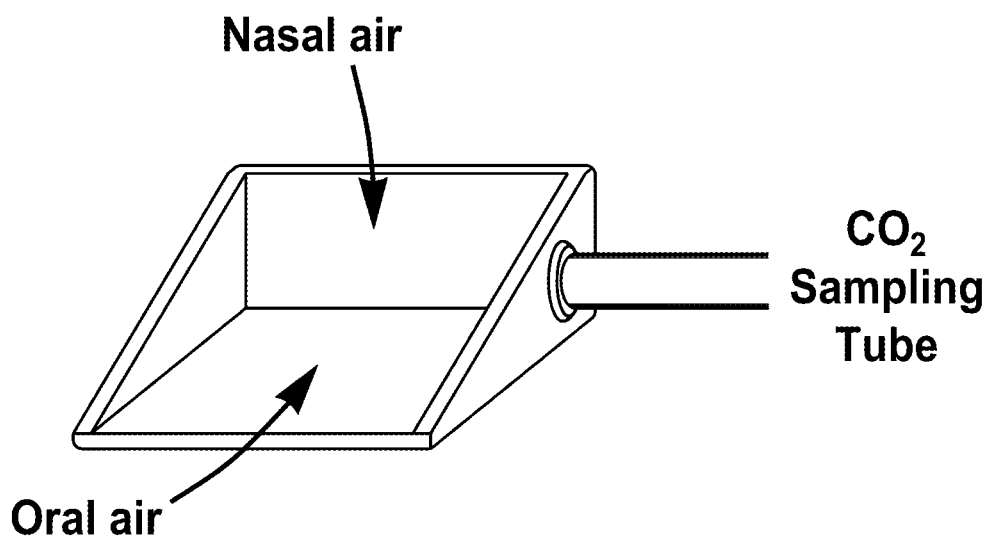
FIG. 4 is an illustration of a gas delivery and monitoring apparatus according to one implementation using a "basket" shaped area that can efficiently capture exhaled oral or nasal $CO_2$.

As shown in FIG. 4, in some embodiments, the gas delivery and monitoring apparatus uses a "basket" shaped area that can efficiently capture exhaled oral or nasal $CO_2$. In some embodiments, the exhalation capture manifold comprises a basket shaped area for the capture of exhaled oral and/or nasal $CO_2$ though a single capture inlet.

Figure 5:
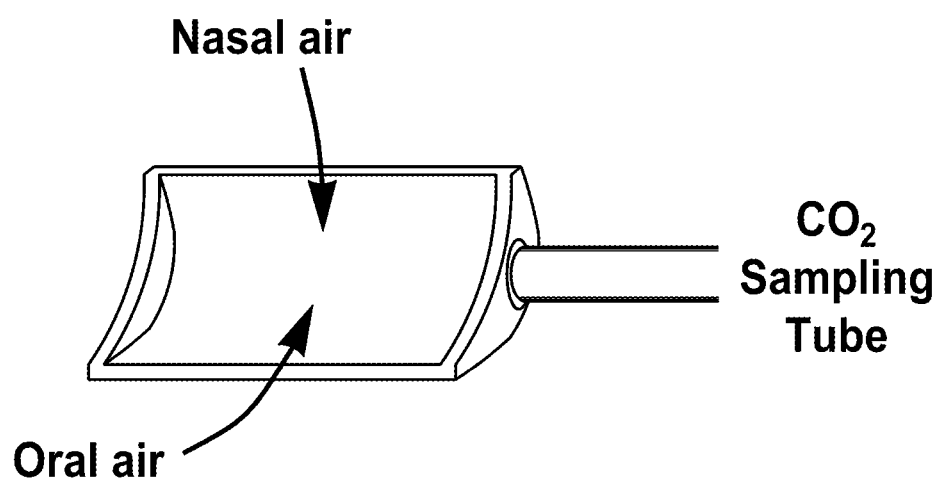
FIG. 5 is an illustration of a gas delivery and monitoring apparatus according to one implementation using a curved "basket" shaped area that can efficiently capture exhaled oral or nasal $CO_2$.

As shown in FIG. 5, in other embodiments, the gas delivery and monitoring apparatus uses a curved "basket" shaped area that can efficiently capture exhaled oral or nasal $CO_2$. In some embodiments, the exhalation capture manifold comprises a curved basket shaped area for the capture of exhaled oral and/or nasal $CO_2$ though a single capture inlet. In some embodiments, the single capture inlet is fluidly connected to the exhalation capture manifold. As shown in FIGS. 4 and 5, the first elongated conduit can be connected to the single capture inlet. In some embodiments, the first elongated conduit is located inside a deformable sheath, allowing the exhalation capture manifold to be positioned in front of the subject's nose and mouth.

Sizeable bite blocks can be added to various embodiments described herein to facilitate the placement of an oral-airway, a laryngeal mask airway, or any other life-saving airway apparatus in case of an emergency. Another application of the bite block is to facilitate the passage of an endoscope in the esophagus or trachea of a patient.

In some embodiments, disclosed herein is a method for the delivery of a first gas and monitoring of a second gas, comprising: providing to a subject an apparatus comprising: a support member having a channel therewithin extending along a longitudinal axis from a proximal end of the channel to a distal end of the channel; a bite block affixed to the support member sized to be inserted within a mouth of a subject; a first elongated conduit defining an exhalation capture flow path extending from an exhalation capture manifold, through the channel from the distal end to the proximal end, and terminating in an outlet port; a second elongated conduit defining a gas delivery flow path extending from an inlet port, through the channel from the proximal end to the distal end, into the bite block, and terminating in a gas delivery port; and wherein the exhalation capture manifold captures exhaled oral and/or nasal carbon dioxide. In some embodiments, the first gas comprises oxygen. In some embodiments, the second gas comprises carbon dioxide. In some embodiments, the subject is under anesthesia.

Figure 6:
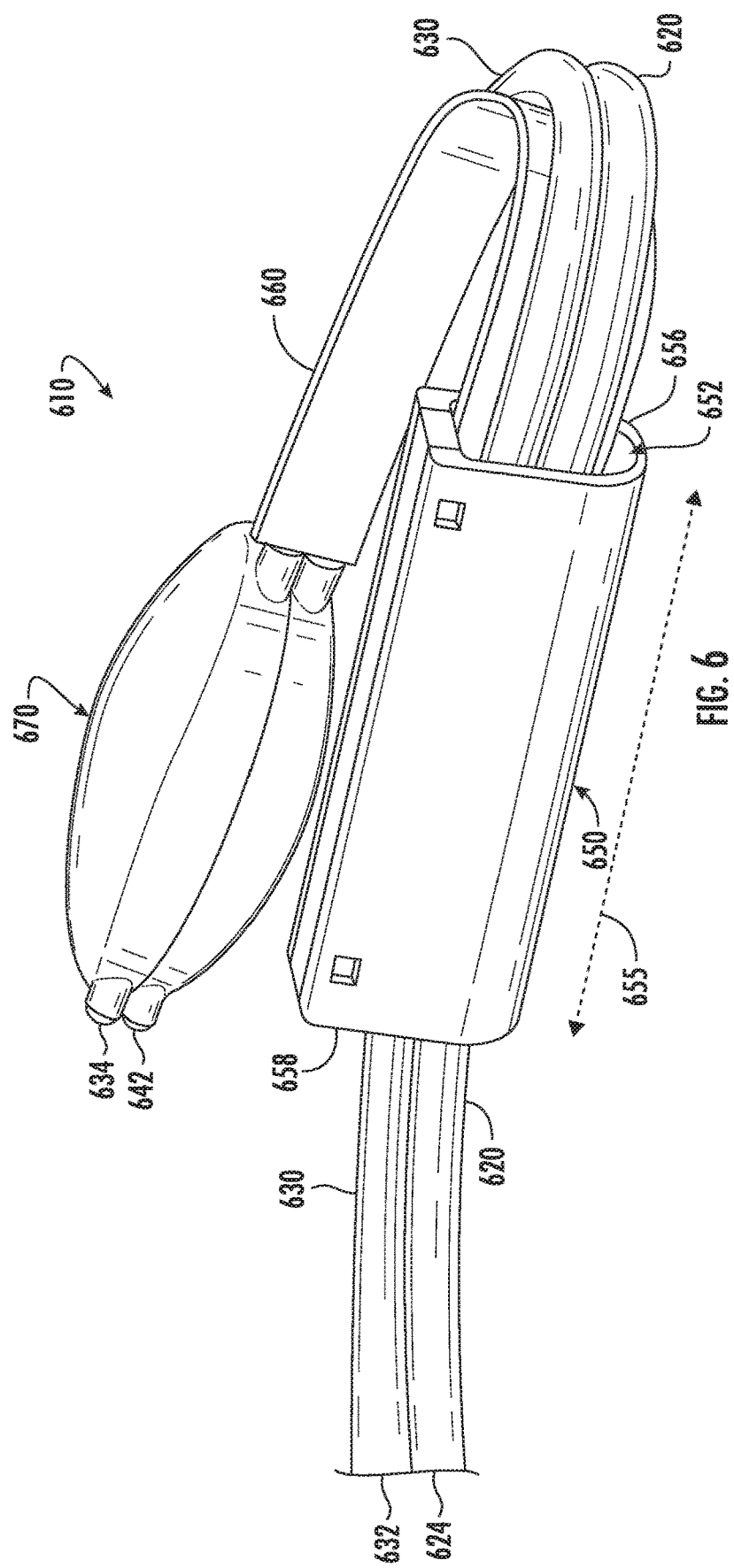
FIG. 6 is a perspective view of a gas delivery and monitoring apparatus, according to another implementation.
Figure 7:
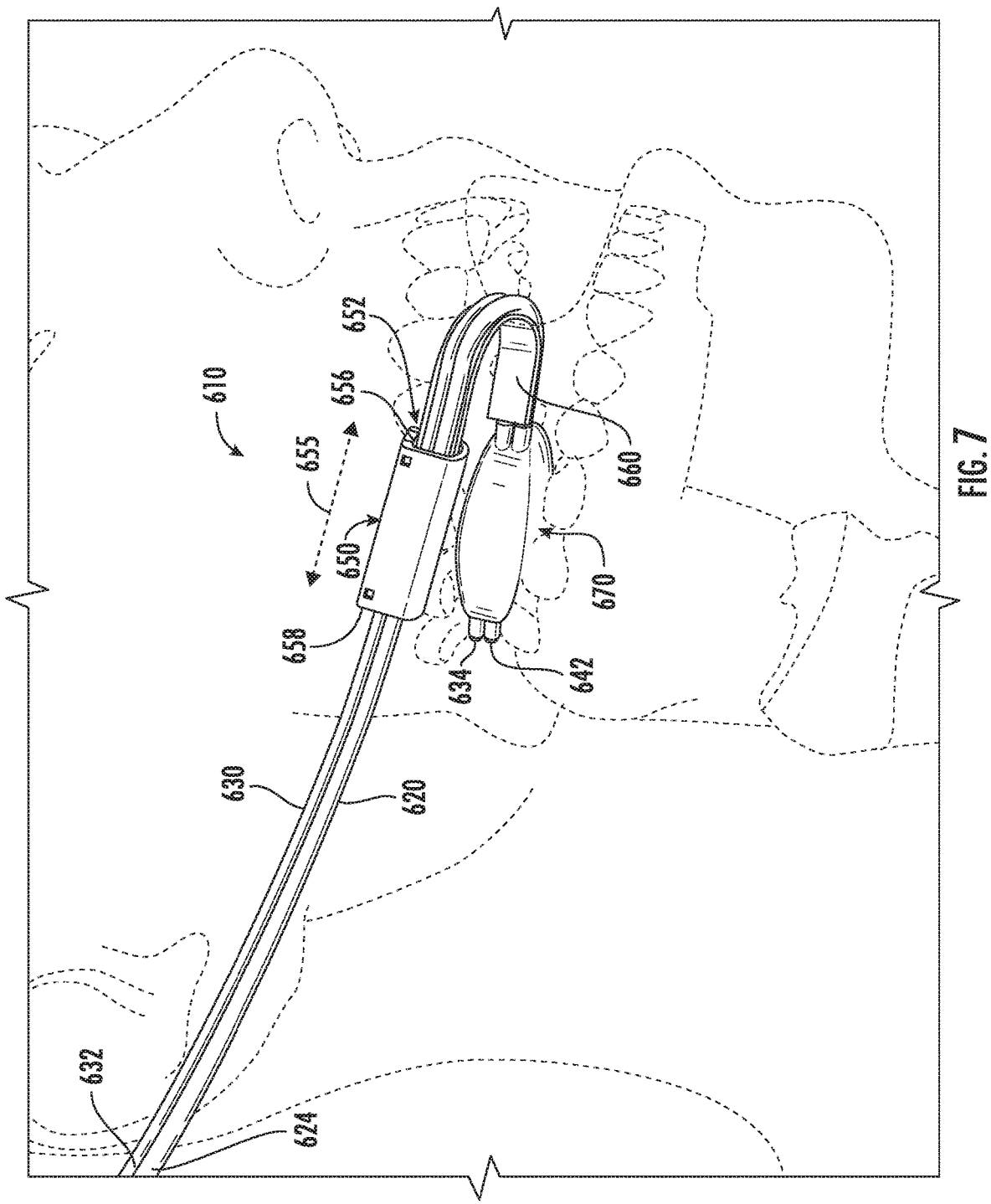
FIG. 7 is a perspective view of a gas delivery and monitoring apparatus of FIG. 6 disposed in the mouth of a subject.

FIGS. 6 and 7 show another embodiment of a gas delivery and monitoring apparatus 610 similar to the gas delivery and monitoring apparatus 10 shown in FIGS. 1-5, but in this embodiment, the first elongated conduit 620 extends through the bite block 670 such that the capture inlet 642 of the first elongated conduit 620 is disposed in the mouth of a subject when the gas delivery and monitoring apparatus 610 is in use. The gas delivery and monitoring apparatus 610 includes a support member 650, a bite block 670, a first elongated conduit 620, a second elongated conduit 630, and a bridge 660. The description of features in the embodiment shown in FIGS. 1-5 can apply to similar features of the embodiment shown in FIGS. 6 and 7.

The support member 650 has a channel 652 therewithin extending along a longitudinal axis 655 from a proximal end 658 of the channel 652 to a distal end 656 of the channel 652. The bridge 660 connects the bite block 670 to the support member 650. The bridge 660 extends away from the support member 650 along a transverse plane perpendicular to the longitudinal axis 655 of the support member 650. The bridge 660 is structured to curve around the corner of the mouth of a subject, and the bite block 670 is sized to be inserted within a mouth of the subject. The support member 650, bite block 670, and bridge 660 shown in FIGS. 6 and 7 are mechanically connected to each other. However, in other embodiments, at least a portion of each of the support member 650, bite block 670, and bridge 660 are integrally formed.

The bridge 660 positions the bite block 670 a first minimum distance from the support member 650 such that the support member 650 and the bite block 670 are simultaneously positionable on opposite sides of the cheek of the subject. The first minimum distance is based on the thickness of a subject's cheek. Therefore, in some embodiments, this first minimum distance is about 1 to 3 cm, including about 1.0, 1.5, 2.0, 2.5, or 3.0 cm. The bridge 660 is also preferably deformable to a second minimum distance from the support member 650 to adjust for the size and shape of the subject's mouth and cheek. In these embodiments, the deformable distance (in a direction away from the support member) can be about 0.1 to 2 cm. In some embodiments, deformation of the bridge 660 also provides spring tension to secure the bite block 670 within the mouth of the subject.

The first elongated conduit 620 defines an exhalation capture flow path. The second elongated conduit 630 defines a gas delivery flow path terminating in an inlet port 632 that is fluidly-connectable to a source of pressurized oxygen. Both the first elongated conduit 620 and the second elongated conduit 630 extend through the channel 652 of the support member 650 similar to the embodiment shown in FIG. 1. However, in the embodiment shown in FIGS. 6 and 7, both the first elongated conduit 620 and the second elongated conduit 630 extend through the bite block 670 such that the capture inlet 642 of the first elongated conduit 620 and the gas delivery port 634 of the second elongated conduit 630 terminate in the mouth of the subject when the gas delivery and monitoring apparatus 610 is in use. To facilitate the first elongated conduit 620 extending through the bite block 670, the bridge 660 is sized such that both the first elongated conduit 620 and the second elongated conduit 630 are extendable along the surface of the bridge 660 to prevent the conduits 620, 630 from kinking when bending around the corner of the mouth of the subject.

Each of the first elongated conduit 620 and second elongated conduit 630 can be made from a flexible elastomeric material that is not gas-permeable. Either of these conduits 620, 630 can also be coated or sheathed with another material to provide additional properties, such as rigidity and deformability. In particular embodiments, the first elongated conduit 620 is encased in a deformable sheath 625 that can be articulated. In some embodiments, the sheath 625 is a plastic tube with a co-extruded metal wire that allows the tube to be bent and hold its shape.

The inner diameters of the first elongated conduit 620 and second elongated conduit 630 can be selected based on desired air pressures. For example, in some embodiments, the first elongated conduit 620 has an inner diameter of about 2 to 4 mm. In some embodiments, the second elongated conduit 630 has an inner diameter of about 2 to 8 mm.

Although FIGS. 6 and 7 show the support member 650 having a channel 652 therewithin, in some embodiments, the support member 650 does not have a channel 652, and the first elongated conduit 620 and the second elongated conduit 630 do not extend through the support member 650.

Figure 8:
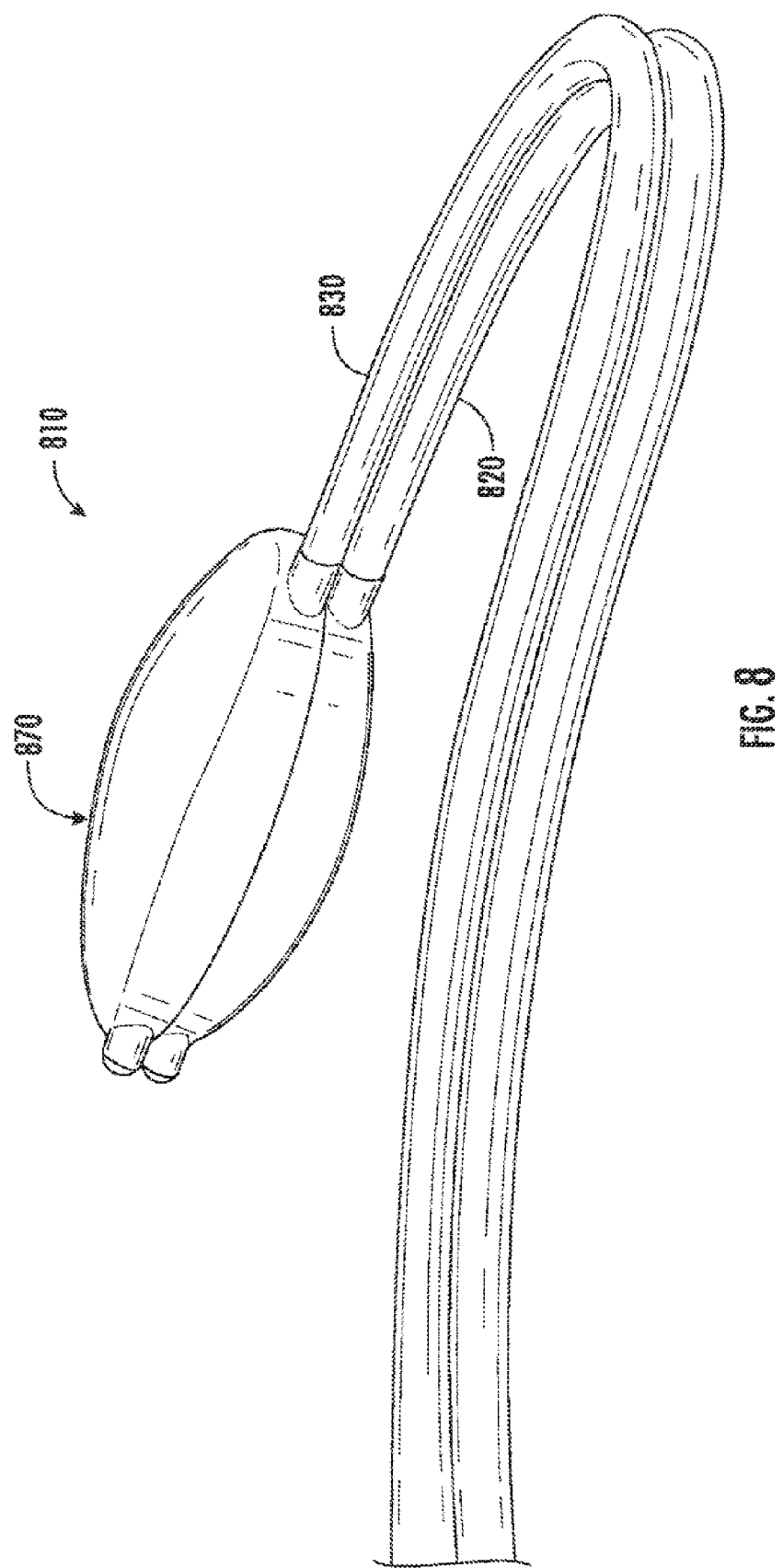
FIG. 8 is a perspective view of a gas delivery and monitoring apparatus, according to another implementation.
Figure 9:
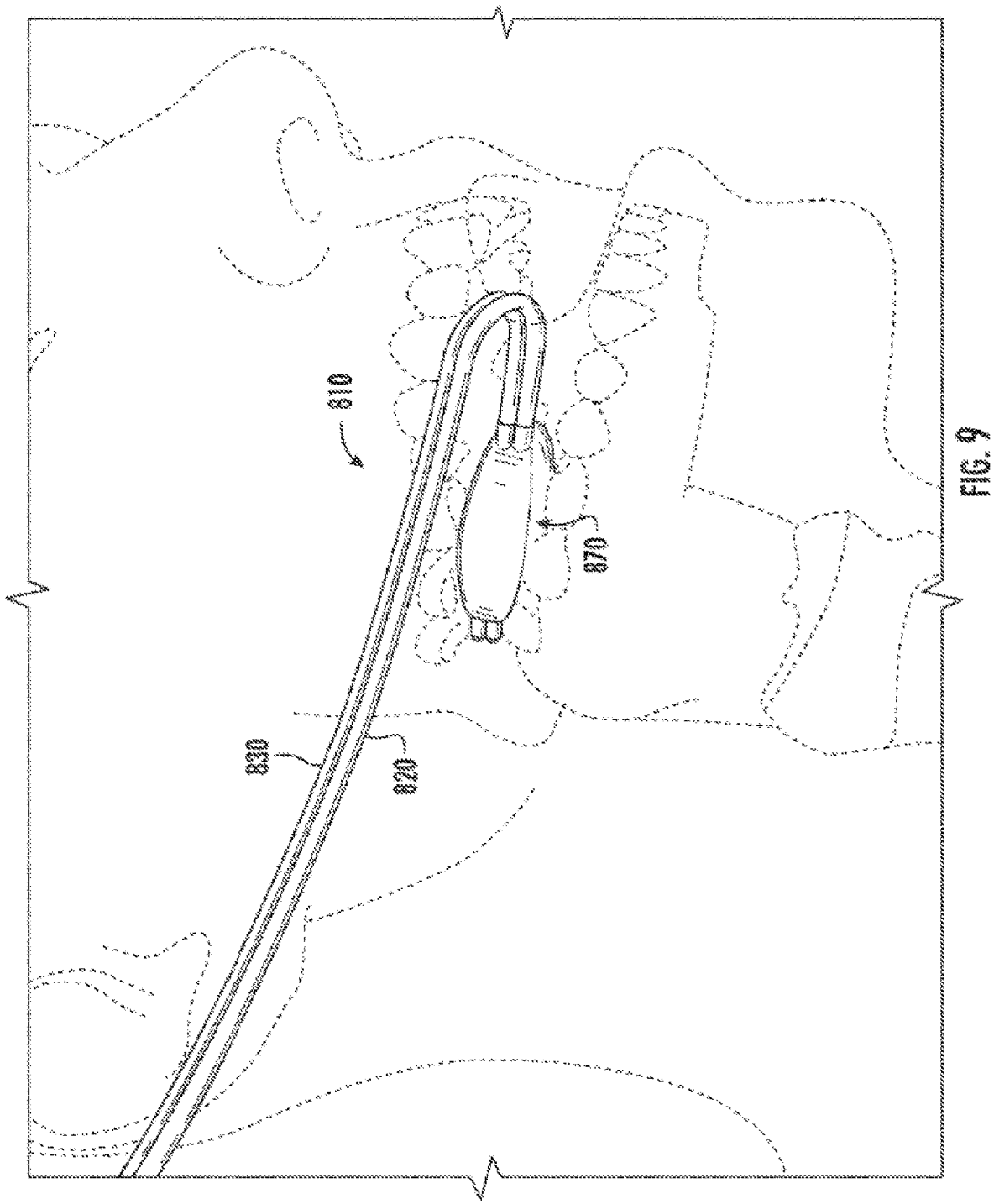
FIG. 9 is a perspective view of a gas delivery and monitoring apparatus of FIG. 8 disposed in the mouth of a subject.

FIGS. 8 and 9 shows another embodiment of a gas delivery and monitoring apparatus 810 similar to the embodiment shown in FIGS. 6 and 7, but in this embodiment, the device does not include a support member or a bridge. Rather, a portion of the first elongated conduit 820 and a portion of the second elongated conduit 830 are rigid and are structured in a U-shape, similar to the shape in which the flexible conduits 620, 630 of the embodiment shown in FIGS. 6 and 7 are held by the support member 650 and the bridge 660. The rigid portions of the first elongated conduit 820 and the second elongated conduit 830 positions the bite block 870 a first minimum distance from the first elongated conduit 820 and the second elongated conduit 830 such that the conduits 820, 830 and the bite block 870 are simultaneously positionable on opposite sides of the cheek of the subject.

Figure 10:
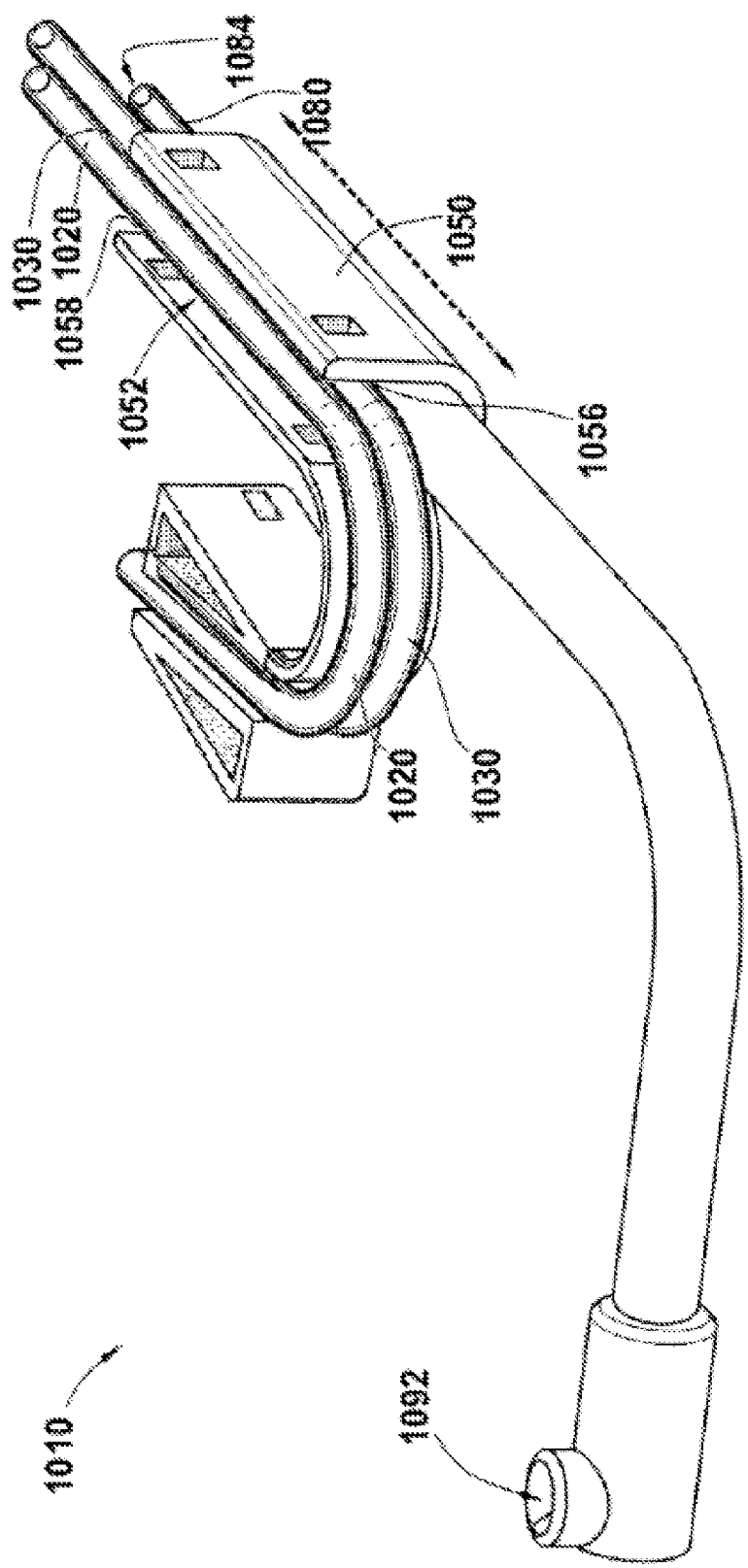
FIG. 10 is a perspective view of a gas delivery and monitoring apparatus, according to another implementation

FIG. 10 shows another embodiment of a gas delivery and monitoring apparatus 1010 having a first elongated conduit 1020 and a second elongated conduit 1030 similar to the embodiment shown in FIGS. 6 and 7, but in this embodiment, the device includes a third elongated conduit 1080 for monitoring nasal exhalation. The description of features in the embodiment shown in FIGS. 1-8 can apply to similar features of the embodiment shown in FIG. 10.

The third elongated conduit 1080 is similar to the first elongated conduit 20 of the embodiment shown in FIGS. 1-5. The third elongated conduit 1080 defines a nasal exhalation capture flow path extending from a secondary capture inlet 1092, through the channel 1052 of the support member 1050 from the distal end 1056 to the proximal end 1058, and terminating in a secondary outlet port 1084. The third elongated conduit 1080 extends from the distal end 1056 of the channel 1052 such that a distance between the distal end 1056 of the channel 1052 and the secondary capture inlet 1092 is about 4 to 8 cm.

The third elongated conduit 1080 is made from a flexible elastomeric material that is not gas-permeable and is encased in a deformable sheath. The third elongated conduit 1080 has an inner diameter of 2 to 4 mm, which can be selected based on desired air pressures.

A number of embodiments of the invention have been described. Nevertheless, it will be understood that various modifications may be made without departing from the spirit and scope of the invention.

Disclosed are materials, systems, devices, compositions, and components that can be used for, can be used in conjunction with, can be used in preparation for, or are products of the disclosed methods, systems and devices. These and other components are disclosed herein, and it is understood that when combinations, subsets, interactions, groups, etc. of these components are disclosed that while specific reference of each various individual and collective combinations and permutations of these components may not be explicitly disclosed, each is specifically contemplated and described herein.

What is claimed is:

1. A gas delivery and monitoring apparatus, comprising:
   (a) a support member having a longitudinal axis, a proximal end, and a distal end opposite and spaced apart from the proximal end;
   (b) a bite block sized to be disposed within a mouth of a subject between at least one tooth of an upper jaw of the subject and at least one tooth of a lower jaw of the subject, the bite block having a proximal end and a distal end opposite and spaced apart from the proximal end,
   (c) a first elongated conduit defining an exhalation capture flow path extending from a capture inlet at the distal end of the bite block and terminating in an outlet port;
   (d) a second elongated conduit defining a gas delivery flow path extending from an inlet port into the bite block, and terminating in a gas delivery port at the distal end of the bite block such that both the gas delivery port and capture inlet are located in the mouth of the subject when the bite block is inserted in the mouth of the subject during use; and
   (e) a bridge extending between the proximal end of the bite block and the proximal end of the support member, wherein the bridge has a curvature that extends the bridge around a corner of the mouth of the subject when the bite block is disposed within the mouth of the subject between the at least one tooth of the upper jaw of the subject and the at least one tooth of the lower jaw of the subject such that the distal end of the support member and the distal end of the bite block are simultaneously positioned on opposite sides of a cheek of the subject and posterior to the corner of the mouth of the subject,
   wherein a portion of the first elongated conduit between the bite block and the support member and a portion of the second elongated conduit between the bite block and the support member follows the curvature of the bridge.

2. The apparatus of claim 1, wherein the support member has a channel therewithin extending along the longitudinal axis from a proximal end of the channel to a distal end of the channel.

3. The apparatus of claim 2, further comprising a third elongated conduit defining a nasal exhalation capture flow path extending from a secondary capture inlet, through the channel from the distal end to the proximal end and terminating in a secondary outlet port.

4. The apparatus of claim 3, wherein the third elongated conduit is encased in a deformable sheath.

5. The apparatus of claim 3, wherein a distance between the distal end of the channel and the secondary capture inlet is about 4 to 8 cm.

6. The apparatus of claim 3, wherein the third elongated conduit has an inner diameter of about 2 to 4 mm.

7. The apparatus of claim 3, wherein the third elongated conduit comprises a flexible elastomeric material that is not gas-permeable.

8. The apparatus of claim 2, wherein the first elongated conduit extends through the channel from the proximal end to the distal end.

9. The apparatus of claim 2, wherein the second elongated conduit extends through the channel from the proximal end to the distal end.

10. The apparatus of claim 1, wherein the bridge extends away from the support member along a transverse plane perpendicular to the longitudinal axis.

11. The apparatus of claim 1, wherein the bridge positions the bite block a first minimum distance from the support member, wherein the first minimum distance is 1 to 3 cm.

12. The apparatus of claim 11, wherein the bridge is deformable to a second minimum distance from the support element.

13. The apparatus of claim 12, wherein the second minimum distance is 1 to 3 cm.

14. The apparatus of claim 12, wherein the bridge provides spring tension to secure the bite block within the mouth of the subject.

15. The apparatus of claim 1, wherein the second elongated conduit extends through the bite block to terminate in the gas delivery port.

16. The apparatus of claim 1, wherein the first elongated conduit comprises an elastomeric material that is not gas-permeable.

17. The apparatus of claim 1, wherein the second elongated conduit comprises an elastomeric material that is not gas-permeable.

18. The apparatus of claim 1, wherein the inlet port is fluidly-connectable to a source of pressurized oxygen.

19. The apparatus of claim 1, wherein at least a portion of each of the support member, bite block, and bridge are integrally formed.

20. The apparatus of claim 1, wherein the support member, bite block, and bridge are mechanically connected.

21. The apparatus of claim 1, wherein the first elongated conduit has an inner diameter of about 2 to 4 mm.

22. The apparatus of claim 1, wherein the second elongated conduit has an inner diameter of about 2 to 8 mm.

* * * * *